(12) United States Patent
Budzik et al.

(10) Patent No.: US 9,044,512 B2
(45) Date of Patent: Jun. 2, 2015

(54) AMINO ALCOHOL CATIONIC LIPIDS FOR OLIGONUCLEOTIDE DELIVERY

(71) Applicant: Sirna Therapeutics, Inc., Cambridge, MA (US)

(72) Inventors: Brian W. Budzik, Perkiomenville, PA (US); Steven L. Colletti, Princeton Junction, NJ (US); Darla Danile Seifried, Lansdale, PA (US); Matthew G. Stanton, Marlton, NJ (US); Lu Tian, Jamison, PA (US)

(73) Assignee: SIRNA THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 14/325,951

(22) Filed: Jul. 8, 2014

(65) Prior Publication Data

US 2014/0323548 A1    Oct. 30, 2014

Related U.S. Application Data

(63) Continuation of application No. 13/699,451, filed as application No. PCT/US2011/036944 on Nov. 21, 2012, now Pat. No. 8,802,863.

(60) Provisional application No. 61/347,640, filed on May 24, 2010.

(51) Int. Cl.
| | |
|---|---|
| *A61K 47/18* | (2006.01) |
| *A61K 31/713* | (2006.01) |
| *C07C 217/40* | (2006.01) |
| *C07C 217/28* | (2006.01) |
| *C12N 15/87* | (2006.01) |
| *C07D 263/14* | (2006.01) |

(52) U.S. Cl.
CPC ............... *A61K 47/18* (2013.01); *C07C 217/28* (2013.01); *C07D 263/14* (2013.01); *C12N 15/87* (2013.01); *C07C 217/40* (2013.01); *A61K 31/713* (2013.01)

(58) Field of Classification Search
None
See application file for complete search history.

(56) References Cited

U.S. PATENT DOCUMENTS

| 7,002,042 B2 | 2/2006 | Gao |
| 8,802,863 B2 * | 8/2014 | Budzik et al. ................. 548/239 |
| 2006/0083780 A1 | 4/2006 | Heyes et al. |
| 2006/0189550 A1 | 8/2006 | Jiang et al. |
| 2006/0240554 A1 | 10/2006 | Chen et al. |
| 2008/0020058 A1 | 1/2008 | Chen et al. |
| 2009/0263407 A1 | 10/2009 | Dande et al. |
| 2009/0285881 A1 | 11/2009 | Dande et al. |

FOREIGN PATENT DOCUMENTS

| WO | WO2009086658 A1 | 7/2009 |
| WO | WO2009127060 A1 | 10/2009 |
| WO | WO2009132131 A1 | 10/2009 |
| WO | WO2010021865 A1 | 2/2010 |
| WO | WO2010042877 A1 | 4/2010 |
| WO | WO2010054384 A1 | 5/2010 |
| WO | WO2010054401 A1 | 5/2010 |
| WO | WO2010054405 A1 | 5/2010 |
| WO | WO2010054406 A1 | 5/2010 |

OTHER PUBLICATIONS

Database CAPLUS on STN, Acc. No. 2007:1311071, Antipina et al., Journal of Physical Chemistry B (2007), 111(49), pp. 13845-13850 (abstract).*
Database CAPLUS on STN, Acc. No. 2007:184015, Antipina et al., Langmuir (2007), 23(7), pp. 3919-3926 (abstract).*
Semple et al. "Rational design of cationic lipids for siRNA delivery." Nature Biotechnology, Epub, 28(2), pp. 172-176, Fig. 2C, DLinDMA, Jan. 17, 2010.
Berge et al. "Pharmaceutical Salts." J. Pharm. Sci. 1977:66, pp. 1-19.
Database CAPLUS on STN, Acc. No. 2007:1311071, Antipina et al., J. Of Physical Chemistry B (2007), 111(49), pp. 13845-13850.
Database CAPLUS on STN, Acc. No. 2007:184015, Antipina et al., Langmuir (2007), 23(7), pp. 3919-3926.

* cited by examiner

*Primary Examiner* — Brian J Davis
(74) *Attorney, Agent, or Firm* — Nixon Peabody LLP

(57) ABSTRACT

The instant invention provides for novel cationic lipids that can be used in combination with other lipid components such as cholesterol and PEG-lipids to form lipid nanoparticles with oligonucleotides. It is an object of the instant invention to provide a cationic lipid scaffold that is more efficacious than traditional cationic lipids. The present invention employs amino alcohols to enhance the efficiency of in vivo delivery of siRNA.

8 Claims, 1 Drawing Sheet

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence -continued

```
<220> FEATURE:
<223> OTHER INFORMATION: Synthetic
<221> NAME/KEY: misc_feature
<222> LOCATION: (1)...(1)
<223> OTHER INFORMATION: 2'-deoxy
<221> NAME/KEY: misc_feature
<222> LOCATION: (2)...(2)
<223> OTHER INFORMATION: 2'-fluoro
<221> NAME/KEY: misc_feature
<222> LOCATION: (3)...(6)
<223> OTHER INFORMATION: 2'-deoxy
<221> NAME/KEY: misc_feature
<222> LOCATION: (7)...(8)
<223> OTHER INFORMATION: 2'-fluoro
<221> NAME/KEY: misc_feature
<222> LOCATION: (9)...(9)
<223> OTHER INFORMATION: 2'-deoxy
<221> NAME/KEY: misc_feature
<222> LOCATION: (10)...(10)
<223> OTHER INFORMATION: 2'-fluoro
<221> NAME/KEY: misc_feature
<222> LOCATION: (11)...(17)
<223> OTHER INFORMATION: 2'-deoxy
<221> NAME/KEY: misc_feature
<222> LOCATION: (18)...(18)
<223> OTHER INFORMATION: 2'-fluoro
<221> NAME/KEY: misc_feature
<222> LOCATION: (19)...(21)
<223> OTHER INFORMATION: 2'-deoxy

<400> SEQUENCE: 1
auaaggcuau gaagagauat t                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic
<221> NAME/KEY: misc_feature
<222> LOCATION: (1)...(3)
<223> OTHER INFORMATION: ribose
<221> NAME/KEY: misc_feature
<222> LOCATION: (4)...(9)
<223> OTHER INFORMATION: 2'-fluoro
<221> NAME/KEY: misc_feature
<222> LOCATION: (10)...(10)
<223> OTHER INFORMATION: 2'-o-methyl
<221> NAME/KEY: misc_feature
<222> LOCATION: (11)...(11)
<223> OTHER INFORMATION: 2'-fluoro
<221> NAME/KEY: misc_feature
<222> LOCATION: (12)...(13)
<223> OTHER INFORMATION: 2'-o-methyl
<221> NAME/KEY: misc_feature
<222> LOCATION: (14)...(17)
<223> OTHER INFORMATION: 2'-fluoro
<221> NAME/KEY: misc_feature
<222> LOCATION: (18)...(18)
<223> OTHER INFORMATION: 2'-o-methyl
<221> NAME/KEY: misc_feature
<222> LOCATION: (19)...(19)
<223> OTHER INFORMATION: 2'-fluoro
<221> NAME/KEY: misc_feature
<222> LOCATION: (20)...(21)
<223> OTHER INFORMATION: 2'-o-methyl

<400> SEQUENCE: 2
uuuauuccga uacuucucua u                                              21

<210> SEQ ID NO 3
<211> LENGTH: 21
<212> TYPE: DNA
<213> ORGANISM: Artificial Sequence
<220> FEATURE:
```

```
<223> OTHER INFORMATION: Synthetic
<221> NAME/KEY: misc_feature
<222> LOCATION: (1)...(4)
<223> OTHER INFORMATION: 2'-fluoro
<221> NAME/KEY: misc_feature
<222> LOCATION: (5)...(6)
<223> OTHER INFORMATION: 2'-deoxy
<221> NAME/KEY: misc_feature
<222> LOCATION: (7)...(7)
<223> OTHER INFORMATION: 2'-fluoro
<221> NAME/KEY: misc_feature
<222> LOCATION: (8)...(9)
<223> OTHER INFORMATION: 2'-deoxy
<221> NAME/KEY: misc_feature
<222> LOCATION: (10)...(14)
<223> OTHER INFORMATION: 2'-fluoro
<221> NAME/KEY: misc_feature
<222> LOCATION: (15)...(18)
<223> OTHER INFORMATION: 2'-deoxy
<221> NAME/KEY: misc_feature
<222> LOCATION: (19)...(19)
<223> OTHER INFORMATION: 2'-fluoro
<221> NAME/KEY: misc_feature
<222> LOCATION: (20)...(21)
<223> OTHER INFORMATION: 2'-deoxy

<400> SEQUENCE: 3
cuuuaacaau uccugaaaut t                                        21

<210> SEQ ID NO 4
<211> LENGTH: 21
<212> TYPE: RNA
<213> ORGANISM: Artificial Sequence
<220> FEATURE:
<223> OTHER INFORMATION: Synthetic
<221> NAME/KEY: misc_feature
<222> LOCATION: (1)...(6)
<223> OTHER INFORMATION: 2'-O-methyl
<221> NAME/KEY: misc_feature
<222> LOCATION: (7)...(8)
<223> OTHER INFORMATION: 2'-fluoro
<221> NAME/KEY: misc_feature
<222> LOCATION: (9)...(9)
<223> OTHER INFORMATION: 2'-O-methyl
<221> NAME/KEY: misc_feature
<222> LOCATION: (10)...(11)
<223> OTHER INFORMATION: 2'-fluoro
<221> NAME/KEY: misc_feature
<222> LOCATION: (12)...(16)
<223> OTHER INFORMATION: 2'-O-methyl
<221> NAME/KEY: misc_feature
<222> LOCATION: (17)...(18)
<223> OTHER INFORMATION: 2'-fluoro
<221> NAME/KEY: misc_feature
<222> LOCATION: (19)...(21)
<223> OTHER INFORMATION: ribose

<400> SEQUENCE: 4
uugaaauugu uaaggacuuu a                                        21
```

AMINO ALCOHOL CATIONIC LIPIDS FOR OLIGONUCLEOTIDE DELIVERY

CROSS REFERENCE TO RELATED APPLICATIONS

This application is a Continuation of U.S. patent application Ser. No. 13/699,451, filed Nov. 21, 2012, which is 35 U.S.C. §371 National Phase Entry Application of International Application No. PCT/US2011/036944 filed May 18, 2011, which designates the U.S., and which claims benefit under 35 U.S.C. §119(e) of the U.S. Provisional Application No. 61/347,640, filed May 24, 2010, the content of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy is named 13699451.txt and is 3178 bytes in size.

BACKGROUND OF THE INVENTION

The present invention relates to novel cationic lipids that can be used in combination with other lipid components such as cholesterol and PEG-lipids to form lipid nanoparticles with oligonucleotides, to facilitate the cellular uptake and endosomal escape, and to knockdown target mRNA both in vitro and in vivo.

Cationic lipids and the use of cationic lipids in lipid nanoparticles for the delivery of oligonucleotides, in particular siRNA and miRNA, have been previously disclosed. Lipid nanoparticles and use of lipid nanoparticles for the delivery of oligonucleotides, in particular siRNA and miRNA, has been previously disclosed. Oligonucleotides (including siRNA and miRNA) and the synthesis of oligonucleotides has been previously disclosed. (See US patent applications: US 2006/0083780, US 2006/0240554, US 200810020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al., Rational design of cationic lipids for siRNA delivery, Nature Biotechnology, published online 17 Jan. 2010; doi: 10.1038/nbt.1602.

Traditional cationic lipids such as DLinDMA have been employed for siRNA delivery to liver but suffer from non-optimal delivery efficiency. It is an object of the instant invention to provide a cationic lipid scaffold that demonstrates enhanced efficacy. The present invention employs amino alcohols to enhance the efficiency of in vivo delivery of siRNA.

SUMMARY OF THE INVENTION

The instant invention provides for novel cationic lipids that can be used in combination with other lipid components such as cholesterol and PEG-lipids to form lipid nanoparticles with oligonucleotides. It is an object of the instant invention to provide a cationic lipid scaffold that is more efficacious than traditional cationic lipids. The present invention employs amino alcohols to enhance the efficiency of in vivo delivery of siRNA.

DETAILED DESCRIPTION OF THE INVENTION

Figure 1:
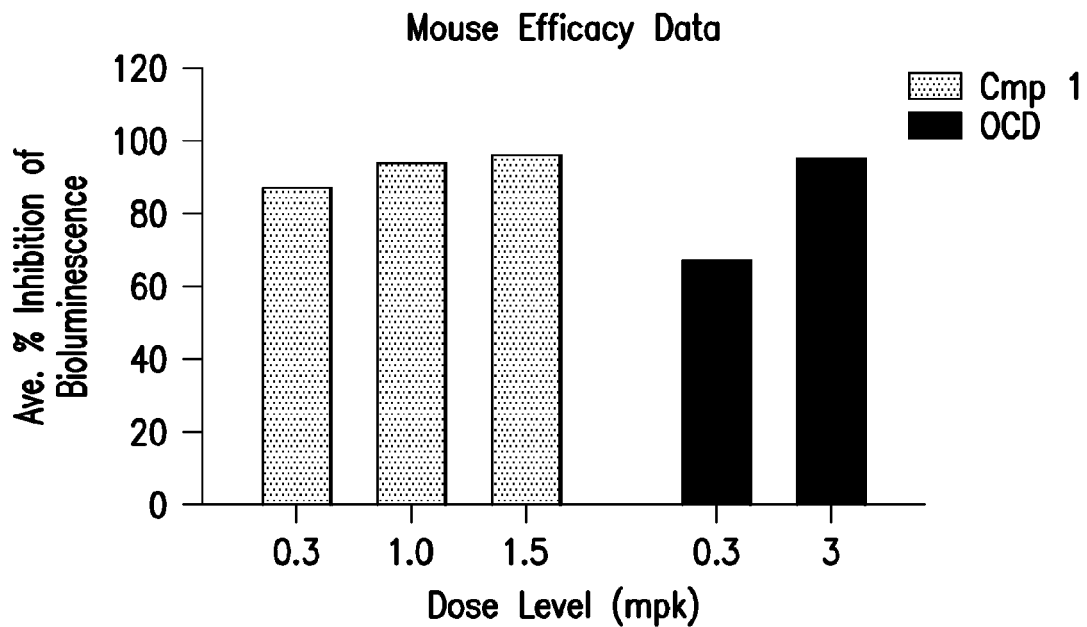
FIG. 1: LNP (Compound 1) efficacy in mice.

The various aspects and embodiments of the invention are directed to the utility of novel cationic lipids useful in lipid nanoparticles to deliver oligonucleotides, in particular, siRNA and miRNA, to any target gene. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al., Rational design of cationic lipids for siRNA delivery, Nature Biotechnology, published online 17 Jan. 2010; doi: 10.1038/nbt.1602.

The cationic lipids of the instant invention are useful components in a lipid nanoparticle for the delivery of oligonucleotides, specifically siRNA and miRNA.

In a first embodiment of this invention, the cationic lipids are illustrated by the Formula A:

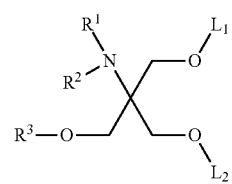

A wherein:

$R^1$ and $R^2$ are independently selected from H, $(C_1-C_6)$ alkyl, heterocyclyl and polyamine, wherein said alkyl, heterocyclyl and polyamine are optionally substituted with one to three substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three substituents selected from R';

$R^3$ is selected from. H and $(C_1-C_6)$alkyl, wherein said alkyl is optionally substituted with one to three substituents selected from R', or $R^3$ can be taken together with $R^1$ to form a monocyclic heterocycle with 4-7 members optionally containing, in addition to the nitrogen, one or two additional heteroatoms selected from N, O and S, said monocyclic heterocycle is optionally substituted with one to three substituents selected from $R^1$;

R' is independently selected from halogen, R", OR", SR", CN, $CO_2R"$ and $CON(R")_2$;

R" is independently selected from H and $(C_1-C_6)$alkyl, wherein said alkyl is optionally substituted with halogen and OH;

$L_1$ is selected from $C_4-C_{22}$ alkyl and $C_4-C_{22}$ alkenyl, said alkyl and alkenyl are optionally substituted with R'; and $L_2$ is selected from $C_4-C_{22}$ alkyl and $C_4-C_{22}$ alkenyl, said alkyl and alkenyl are optionally substituted with $R^{40}$;

or any pharmaceutically acceptable salt or stereoisomer thereof.

In a second embodiment, the invention features a compound having Formula A, wherein:
$R^1$ and $R^2$ are each H;
$R^3$ is H;
$L_1$ is selected from $C_4$-$C_{22}$ alkyl and $C_4$-$C_{22}$ alkenyl; and
$L_2$ is selected from $C_4$-$C_{22}$ alkyl and $C_4$-$C_{22}$ alkenyl;
or any pharmaceutically acceptable salt or stereoisomer thereof.

Specific cationic lipids are:
2-amino-3-[(9Z,12Z)-octadeca-9,12-dien-1-yloxy]-2-{[(9Z,12Z)-octadeca-9,12-dien-1-yloxy]methyl}propan-1-ol (Compound 1);
2-amino-3-[(9Z)-octadec-9-en-1-yloxy]-2-{[(9Z)-octadec-9-en-1-yloxy]methyl}propan-1-ol (Compound 2);
2-amino-3-[(9Z,12Z)-octadeca-9,12-dien-1-yloxy]-2-[(octyloxy)methyl]propan-1-ol (Compound 3); and
2-(dimethylamino)-3-[(9Z,12Z)-octadeca-9,12-dien-1-yloxy]-2-{[(9Z,12Z)-octadeca-9,12-dien-1-ylox]methyl}propan-1-ol (Compound 4);
or any pharmaceutically acceptable salt or stereoisomer thereof.

In another embodiment, the cationic lipids disclosed are useful in the preparation of lipid nanoparticles.

In another embodiment, the cationic lipids disclosed are useful components in a lipid nanoparticle for the delivery of oligonucleotides.

In another embodiment, the cationic lipids disclosed are useful components in a lipid nanoparticle for the delivery of siRNA and miRNA.

In another embodiment, the cationic lipids disclosed are useful components in a lipid nanoparticle for the delivery of siRNA.

The cationic lipids of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the cationic lipids disclosed herein may exist as tautomers and both tautomeric forms are intended to be encompassed by the scope of the invention, even though only one tautomeric structure is depicted.

It is understood that substituents and substitution patterns on the cationic lipids of the instant invention can be selected by one of ordinary skill in the art to provide cationic lipids that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

It is understood that one or more Si atoms can be incorporated into the cationic lipids of the instant invention by one of ordinary skill in the art to provide cationic lipids that are chemically stable and that can be readily synthesized by techniques known in the art from readily available starting materials.

In the compounds of Formula A, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula A. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula A can be prepared without undue experimentation by conventional techniques well known to those skilled in the art or by processes analogous to those described in the Scheme and Examples herein using appropriate isotopically-enriched reagents and/or intermediates.

As used herein, "alkyl" means a saturated aliphatic hydrocarbon having the specified number of carbon atoms.

As used herein, "alkenyl" means an unsaturated aliphatic hydrocarbon having the specified number of carbon atoms.

As used herein, "heterocyclyl" or "heterocycle" means a 4- to 10-membered aromatic or nonaromatic heterocycle containing from 1 to 4 heteroatoms selected from the group consisting of O, N and S, and includes bicyclic groups. "1-leterocyclyl" therefore includes, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof all of which are optionally substituted with one to three substituents selected from R".

As used herein, "polyamine" means compounds having two or more amino groups. Examples include putrescine, cadaverine, spermidine, and spermine.

As used herein, "halogen" means Br, Cl, F and I.

In an embodiment of Formula A, $R^1$ and $R^2$ are independently selected from H, and $(C_1$-$C_6)$alkyl, wherein said alkyl is optionally substituted with one to three substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three substituents selected from In an embodiment of Formula A, $R^1$ and $R^2$ are independently selected from H, methyl, ethyl and propyl, wherein said methyl, ethyl and propyl is optionally substituted with one to three substituents selected from R', or $R^1$ and $R^2$ can be taken together with the nitrogen to which they are attached to form a monocycle heterocycle with 4-7 members optionally containing, in addition to the nitrogen, one or two additional heteroatoms selected from N, O and S, said monocyclic heterocycle is optionally substituted with one to three substituents selected from R'.

In an embodiment of Formula A, $R^1$ and $R^2$ are independently selected from H, methyl, ethyl and propyl.

In an embodiment of Formula A, $R^1$ and $R^2$ are each H.

In an embodiment of Formula A, $R^3$ is selected from H, methyl, ethyl and propyl, wherein said methyl, ethyl and propyl is optionally substituted with one to three substituents selected from R', or $R^3$ can be taken together with $R^1$ to form a monocycle heterocycle with 4-7 members optionally containing, in addition to the nitrogen, one or two additional heteroatoms selected from N, O and S, said monocycle heterocycle is optionally substituted with one to three substituents selected from R'.

In an embodiment of Formula A, $R^3$ is selected from H, methyl, ethyl and propyl.

In an embodiment of Formula A, $R^3$ is H.

In an embodiment of Formula A, R' is R".

In an embodiment of Formula A, R" is independently selected from H, methyl, ethyl and propyl, wherein said methyl, ethyl and propyl is optionally substituted with halogen and OH.

In an embodiment of Formula A, R" is independently selected from H, methyl, ethyl and propyl.

In an embodiment of Formula A, $L^1$ is selected from $C_4$-$C_{22}$ alkyl and $C_4$-$C_{22}$ alkenyl, which are optionally substituted with halogen and OH.

In an embodiment of Formula A, $L^1$ is selected from $C_4$-$C_{22}$ alkyl and $C_4$-$C_{22}$ alkenyl.

In an embodiment of Formula A, $L_2$ is selected from $C_4$-$C_{22}$ alkyl and $C_4$-$C_{22}$ alkenyl, which are optionally substituted with halogen and OH.

In an embodiment of Formula A, $L_2$ is selected from $C_4$-$C_{22}$ alkyl and $C_4$-$C_{22}$ alkenyl.

In an embodiment of Formula A, "heterocyclyl" is pyrolidine, piperidine, morpholine, imidazole or piperazine.

In an embodiment of Formula A, "monocyclic heterocyclyl" is pyrolidine, piperidine, morpholine, imidazole or piperazine.

In an embodiment of Formula A, "polyamine" is putrescine, cadaverine, spermidine or spermine.

Included in the instant invention is the free form of cationic lipids of Formula A, as well as the pharmaceutically acceptable salts and stereoisomers thereof. Some of the isolated specific cationic lipids exemplified herein are the protonated salts of amine cationic lipids. The term "free form" refers to the amine cationic lipids in non-salt form. The encompassed pharmaceutically acceptable salts not only include the isolated salts exemplified for the specific cationic lipids described herein, but also all the typical pharmaceutically acceptable salts of the free form of cationic lipids of Formula A. The free form of the specific salt cationic lipids described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant cationic lipids can be synthesized from the cationic lipids of this invention which contain a basic or acidic moiety by conventional chemical methods. Generally, the salts of the basic cationic lipids are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the cationic lipids of this invention include the conventional non-toxic salts of the cationic lipids of this invention as formed by reacting a basic instant cationic lipids with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic (TFA) and the like.

When the cationic lipids of the present invention are acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethyl amine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the cationic lipids of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

EXAMPLES

Examples provided are intended to assist in a further understanding of the invention. Particular materials employed, species and conditions are intended to be further illustrative of the invention and not limitative of the reasonable scope thereof. The reagents utilized in synthesizing the cationic lipids are either commercially available or are readily prepared by one of ordinary skill in the art.

Synthesis of the novel cationic lipids is a linear process starting with amino triol (Tris, i). Protection as the acetonide followed by O-alkylation generates iii. Deprotection of the acetonide followed by a second O-alkylation generates amino alcohol lipids of the general formula v.

GENERAL REACTION SCHEME 1

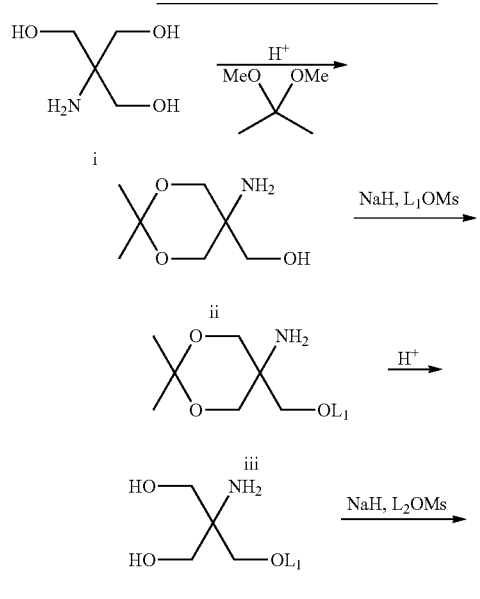

An alternative route to amino alcohol cationic lipids starts with oxazoline protected Tris vi. Alkylation of the alcohols generates intermediate vii which is deprotected in ethanolic HCl to give final products of the general formula viii.

GENERAL REACTION SCHEME 2

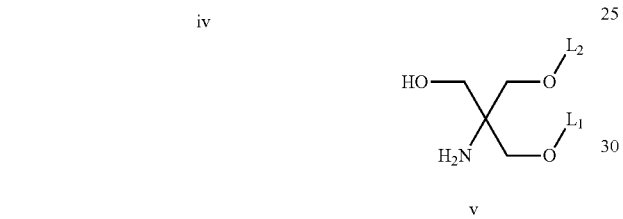

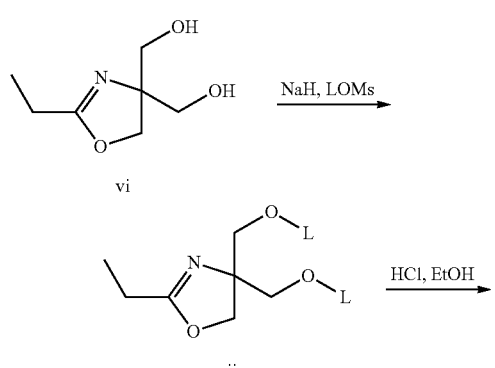

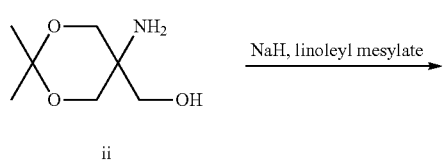

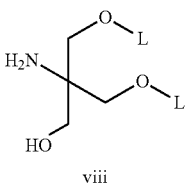

GENERAL REACTION SCHEME 3

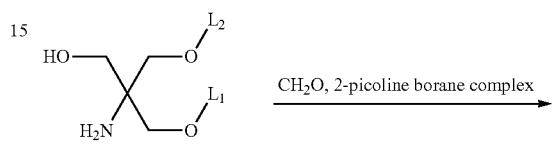

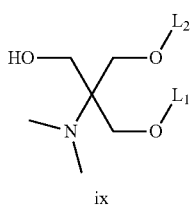

SCHEME 1
2-amino-3-[(9Z,12Z)-octadeca-9,12-dien-1-yloxy]-2-{[(9Z,12Z)-octadeca-9,12-dien-1-yloxy]methyl}propan-1-ol (Compound 1)

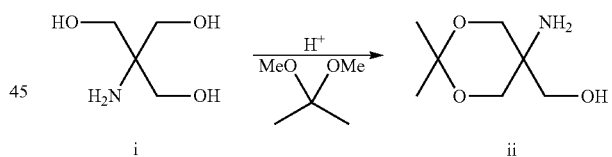

To 160 ml of DMF was added TRIS® HCl (i) (20 g, 127 mmol) and pTsOH (1.8 g, 9.46 mmol). To the reaction solution, 2,2-dimethoxypropane (18 ml, 145 mmol) was added dropwise. After stirring under the argon for 48 hours, DMF was removed in vacuo. The crude product was further purified by flash chromatography ($CH_2Cl_2$/Methanol). The final product (white solid) was 13 grams. LC/MS m/z 162.1.

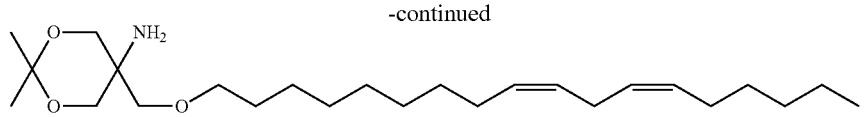

iii

NaH (0.472 g, 19.65 mmol) was added into 250 ml RBF (round bottom flask), followed by addition of toluene (90 ml). In the ice/water bath, compound ii (2.64 g, 16.38 mmol) was added into the reaction system and stirred under argon for 1 hour. Linoleyl mesylate (16.38 mmol) in 10 ml of toluene was added dropwise into the reaction system in the ice/water bath. The reaction system was slowly warmed up to room temperature and then refluxing under the argon. After 5 hours, by LC/MS, the reaction was completed. After cooled down in the ice/water bath, 10 ml of ice cold water was dropped into the reaction system to neutralize the base. The solvent was removed in vacuo and the crude product dissolved into 300 ml of ether and washed by brine (100 ml×3). After dry over sodium sulfate anhydrous, the crude product was concentrated and dry-loaded onto the column and purified ($CH_2Cl_2$/Methanol) to give iii as a colorless oil. LC/MS m/z 410.4.

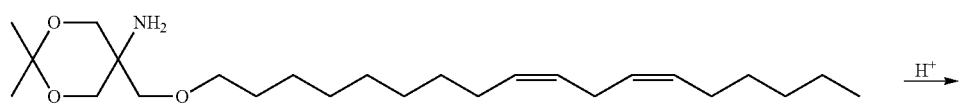

iii

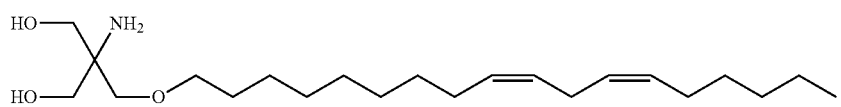

iv

Compound iii (8.0 g, 19.53 mmol) was dissolved into THF (100 ml). 20 ml of 6N HCl (4.93 ml, 60 mmol) was added dropwise into the reaction system at 0° C. After 5 hours, the reaction was complete. The reaction solution was neutralized by addition of saturated sodium bicarbonate and partitioned between water/$CH_2Cl_2$. The crude product was further purified by flash chromatography ($CH_2Cl_2$/Methanol) to give iv as a colorless oil: $^1$H NMR (400 MHz, CDCl3): δ 5.32-5.42 (m, 4H), 3.52 (s, 4H), 3.43 (t, J=6.4 Hz, 2H), 3.41 (s, 2H), 2.78 (t, J=6.4 Hz, 2H), 2.05 (q, J=6.8 Hz, 4H), 1.55-1.58 (m, 2H), 1.30-1.37 (m, 18H), 0.89 (t, J=6.8, 3H); m/z 370.3.

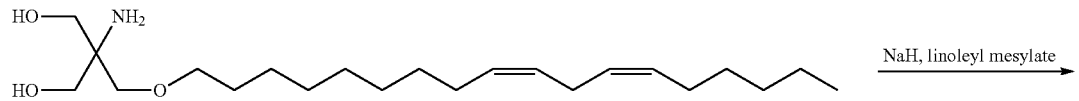

iv

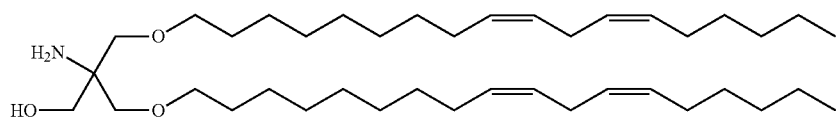

1

NaH (0.186 g, 7.74 mmol) was added into 100 ml RBF, followed by addition of toluene (100 ml). In the ice/water bath, Compound iv (2.2 g, 5.95 mmol) was added into the reaction system and stirred under argon for 1 hour. Lionoleyl mesylate (6.55 mmol) in 10 ml of toluene was added dropwise into the reaction system in the ice/water bath. The reaction system was slowly warmed up to room temperature and then refluxed under the argon. After 4 hours the reaction was cooled to 0° C. and 10 ml of ice cold water was dropped into the reaction system to neutralize the base. The solvent was removed in vacuo and the crude product was partitioned between ether/water then washed by brine (100 ml×3). The organics were dried over sodium sulfate, filtered, and the crude product was concentrated and purified by flash chromatography (CH$_2$Cl$_2$/Methanol) to give 1 as a colorless oil, $^1$H NMR δ (ppm) (CDCl$_3$): 5.41-5.27 (m, 8H), 3.50 (s, 4H), 3.38 (1, 4H), 3.36 (d, 2H), 3.31 (d, 2H), 2.74 (t, 4H), 2.02 (q, 4H), 1.52 (m,4H), 1.29 (m, 36H), 0.85 (t, 6H); LC/MS m/z 618.6.

Scheme 2 (Alternate Synthesis)

2-amino-3 -[(9Z,12Z)-octadeca-9,12-dien-1-yloxy]-2-{[(9Z,12Z)-octadeca-9,12-dien-1-yloxy]methyl}propan-1-ol (Compound 1)

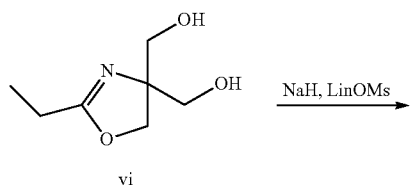

vi

NaH, LinOMs →

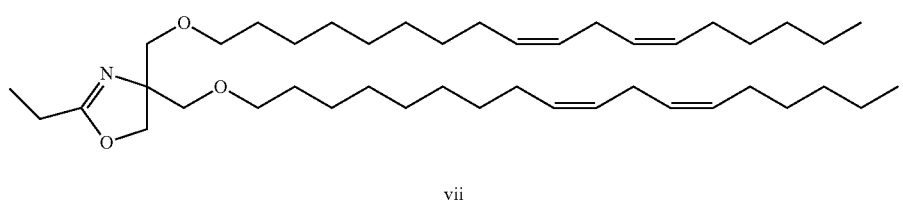

vii

To a stirred solution of sodium hydride (43.3 mmol, 1.7 g) in toluene (140 mL) was added oxazoline diol vi (14.5 mmol, 2.3 g) at 0° C. The resulting mixture was heated to 80° C. for 30 minutes. Triethylamine hydrochloride (2.9 mmol, 0.4 g) was added and the solution stirred for 10 minutes. Linoleyl mesylate (30.3 mmol, 10.3 g) was then added and the reaction was stirred at 80° C. for 16 hours. The reaction was cooled to ambient temperature, quenched with water and partitioned between water and ethyl acetate. The organics were washed with brine, dried over sodium sulfate, filtered and evaporated in vacuo. The crude oil was purified by flash chromatography (silica, 0-10% EtOAc/hexanes) to give 3.5 g of vii as a colorless oil. HRMS: calc'd m/z=656.5976, measured m/z=656.5994.

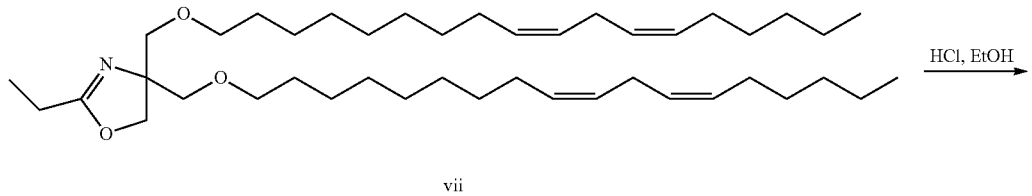

vii

HCl, EtOH →

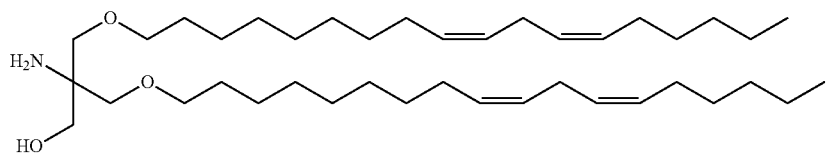

1

To a solution of oxazoline vii (2.2 mmol, 1.4 g) in ethanol (20 mL) was added 6M ethanolic HCl (3.6 mL, 21.6 mmol). The solution turned milky white. The reaction mixture was heated to 70° C. for 48 hours. The reaction was cooled to ambient temperature, neutralized with aqueous ammonium hydroxide and partitioned between water/dichloromethane. The aqueous phase was extracted with 3 portions of dichloromethane. The combined organics were washed with brine, dried over sodium sulfate, filtered and evaporated in vacuo to give 1.5 g of compound 1. Analytical data matched previously reported data above.

Compounds 2 and 3 are novel cationic lipids and were prepared according to the Schemes above.

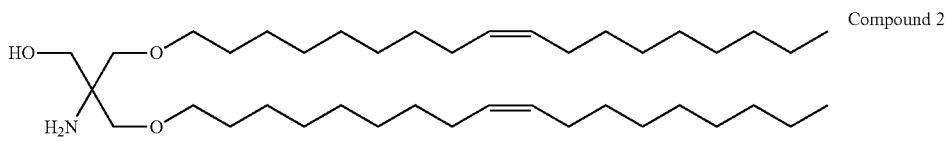 [SMILES: CCCCCCCC/C=C\CCCCCCCCOCC(N)(CO)COCCCCCCCC/C=C\CCCCCCCC]

Compound 2

2-amino-3-[(9Z)-octadec-9-en-1-yloxy]-2-{[(9Z)-octadec-9-en-1-yloxy]methyl}propan-1-ol (Compound 2)

$^1$H NMR (400 MHz, CDCl$_3$): δ 5.33-5.36 (m, 4H), 3.51 (s, 2H), 3.41 (t, J=6.4 Hz, 4H), 3.39 (A of ABq, J=9.2 Hz, 2H), 3.33 (B of ABq, J=9.2 Hz, 2H), 2.02 (q, J=7.5 Hz, 8H), 1.53-1.55 (m, 10H), 1.27-1.29 (m, 40H), 0.88 (t, J=6.8, 6H); LC/MS m/z 622.6.

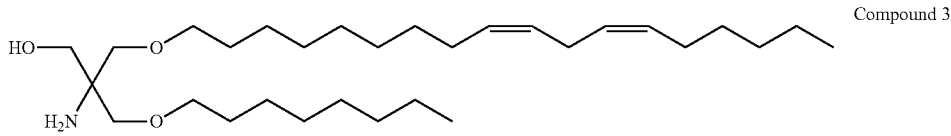 [SMILES: CCCCC/C=C\C/C=C\CCCCCCCCOCC(N)(CO)COCCCCCCCC]

Compound 3

2-amino-3-[(9Z,12Z)-octadeca-9,12-dien-1-yloxy]-2-[(octyloxy)methyl]propan-1-ol (Compound 3)

$^1$H NMR (400 MHz, CDCl$_3$): δ 5.32-5.41 (m, 4H), 3.51 (s, 2H), 3.42 (t, J=6.4 Hz, 4H), 3.39 (A of ABq, J=9.2 Hz, 2H), 3.34 (B of ABq, J=9.2 Hz, 2H), 2.77 (t, J=6.8 Hz, 2H), 2.05 (q, J=6.8 Hz, 4H), 1.52-1.57 (m, 8H), 1.24-1.39 (m, 24H), 0.86-0.91 (m, 6H); LC/MS m/z 482.5.

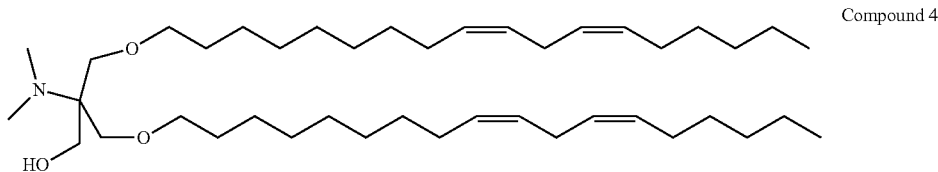 [SMILES: CCCCC/C=C\C/C=C\CCCCCCCCOCC(CO)(COCCCCCCCC/C=C\C/C=C\CCCCC)N(C)C]

Compound 4

2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4)

A solution of 2-amino-3-[(9Z,12Z)-octadeca-9,12-dien-1-yloxy]-2-{[(9Z,12Z)-octadeca-9,12-dien-1-yloxy]methyl}propan-1-ol (2.29 g, 3.7 mmol) and formaldehyde (3.01 g, 37.1 mmol) in THF (25 mL) and acetic acid (6.25 mL) was treated with 2-picoline borane complex (0.79 g, 7.4 mmol). The reaction was stirred at ambient temperature for 1 hour and then partitioned between aqueous citric acid (10%) and ethyl acetate. The aqueous layer was washed with ethyl acetate (3×) and the combined organics were dried over magnesium sulfate, filtered and evaporated in vacuo. Purification by flash chromatography (silica, 0-4% methanol/DCM) to generated Compound 4 as a pale yellow oil.

$^1$H NMR (400 MHz, CDCl$_3$): δ 5.3-5.42 (m, 8H), 3.56 (s, 2H), 3.48 (dd, J=24, 8 Hz, 4H), 3.39 (t, J=5.2 Hz, 4H), 2.78 (t, 4H), 2.39 (s, 6H), 2.05 (q, 8H), 1.55 (m,4H), 1.29 (m, 36H), 0.89 (t, 6H); HRMS (m+H) calc'd: 646.6060, found: 646.6140.

LNP Compositions

The following lipid nanoparticle compositions (LNPs) of the instant invention are useful for the delivery of oligonucleotides, specifically siRNA and miRNA:
Cationic Lipid/Cholesterol/PEG-DMG 56.6/38/5.4;
Cationic Lipid/Cholesterol/PEG-DMG 60/38/2;
Cationic Lipid/Cholesterol/PEG-DMG 673/29/31;
Cationic Lipid/Cholesterol/PEG-DMG 49.3/47/3.7;
Cationic Lipid/Cholesterol/PEG-DMG 50.3/44.3/5.4;
Cationic Lipid/Cholesterol/PEG-C-DMA/DSPC 40/48/2/10; and
Cationic Lipid/Cholesterol/PEG-DMG/DSPC 40/48/2/10.

The synthesis and use of LNPs are known. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al., Rational design of cationic lipids for siRNA delivery, Nature Biotechnology, published online 17 Jan. 2010; doi: 10.1038/nbt.1602.

LNP Process Description:

The Lipid Nano-Particles (LNP) are prepared by an impinging jet process. The particles are formed by mixing lipids dissolved in alcohol with siRNA dissolved in a citrate buffer. The mixing ratio of lipids to siRNA are targeted at 45-55% lipid and 65-45% siRNA. The lipid solution contains a novel cationic lipid of the instant invention, a helper lipid (cholesterol), PEG (e.g. PEG-C-DMA, PEG-DMG) lipid, and DSPC at a concentration of 5-15 mg/mL with a target of 9-12 mg/mL in an alcohol (for example ethanol). The ratio of the lipids has a mole percent range of 25-98 for the cationic lipid with a target of 35-65, the helper lipid has a mole percent range from 0-75 with a target of 30-50, the PEG lipid has a mole percent range from 1-15 with a target of 1-6, and the DSPC has a mole percent range of 0-15 with a target of 0-12. The siRNA solution contains one or more siRNA sequences at a concentration range from 0.3 to 1.0 mg/mL with a target of 0.3-0.9 mg/mL in a sodium citrate buffered salt solution with pH in the range of 3.5-5. The two liquids are heated to a temperature in the range of 15-40° C., targeting 30-40° C., and then mixed in an impinging jet mixer instantly forming the LNP. The teeID has a range from 0.25 to 1.0 mm and a total flow rate from 10-600 mL/min. The combination of flow rate and tubing ID has effect of controlling the particle size of the LNPs between 30 and 200 nm. The solution is then mixed with a buffered solution at a higher pH with a mixing ratio in the range of 1:1 to 1:3 vol:vol but targeting 1:2 vol:vol. This buffered solution is at a temperature in the range of 15-40° C., targeting 30-40° C. The mixed LNPs are held from 30 minutes to 2 hrs prior to an anion exchange filtration step. The temperature during incubating is in the range of 15-40° C., targeting 30-40° C. After incubating the solution is filtered through a 0.8 um filter containing an anion exchange separation step. This process uses tubing Ms ranging from 1 mm ID to 5 mm ID and a flow rate from 10 to 2000 mL/min. The LNPs are concentrated and diafiltered via an ultrafiltration process where the alcohol is removed and the citrate buffer is exchanged for the final buffer solution such as phosphate buffered saline. The ultrafiltration process uses a tangential flow filtration format (TFF). This process uses a membrane nominal molecular weight cutoff range from 30-500 KD. The membrane format can be hollow fiber or flat sheet cassette. The TFF processes with the proper molecular weight cutoff retains the LNP in the retentate and the filtrate or permeate contains the alcohol; citrate buffer; final buffer wastes. The TFF process is a multiple step process with an initial concentration to a siRNA concentration of 1-3 mg/mL. Following concentration, the LNPs solution is diafiltered against the final buffer for 10 -20 volumes to remove the alcohol and perform buffer exchange. The material is then concentrated an additional 1-3 fold. The final steps of the LNP process are to sterile filter the concentrated LNP solution and vial the product.

Analytical Procedure:

1) siRNA Concentration

The siRNA duplex concentrations are determined by Strong Anion-Exchange High-Performance Liquid Chromatography (SAX-HPLC) using Waters 2695 Alliance system (Water Corporation, Milford Mass.) with a 2996 PDA detector. The LNPs, otherwise referred to as RNAi Delivery Vehicles (RDVs), are treated with 0.5% Triton X-100 to free total siRNA and analyzed by SAX separation using a Dionex BioLC DNAPac PA 200 (4×250 mm) column with UV detection at 254 nm. Mobile phase is composed of A: 25 mM NaClO$_4$, 10 mM Tris, 20% EtOH, pH 7.0 and B: 250 mM NaClO$_4$, 10 mM Tris, 20% EtOH, pH 7.0 with liner gradient from 0-15 min and flow rate of 1 ml/min. The siRNA amount is determined by comparing to the siRNA standard curve.

2) Encapsulation Rate

Fluorescence reagent SYBR Gold is employed for RNA quantitation to monitor the encapsulation rate of RDVs. RDVs with or without Triton X-100 are used to determine the free siRNA and total siRNA amount. The assay is performed using a SpectraMax M5e microplate spectrophotometer from Molecular Devices (Sunnyvale, Calif.). Samples are excited at 485 nm and fluorescence emission was measured at 530 nm. The siRNA amount is determined by comparing to the siRNA standard curve.

Encapsulation rate=(1−free siRNA/total siRNA)× 100%

3) Particle Size and Polydispersity

RDVs containing 1 μg siRNA are diluted to a final volume of 3 ml with 1×PBS. The particle size and polydispersity of the samples is measured by a dynamic light scattering method using ZetaPALS instrument (Brookhaven Instruments Corporation, Holtsville, N.Y.). The scattered intensity is measured with He—Ne laser at 25° C. with a scattering angle of 90°.

4) Zeta Potential Analysis

RDVs containing 1 μg siRNA are diluted to a final volume of 2 ml with 1 mM Tris buffer (pH 7.4). Electrophoretic mobility of samples is determined using ZetaPALS instrument (Brookhaven Instruments Corporation, Holtsville, N.Y.) with electrode and He—Ne laser as a light source. The Smoluchowski limit is assumed in the calculation of zeta potentials.

5) Lipid Analysis

Individual lipid concentrations are determined by Reverse Phase High-Performance Liquid Chromatography (RP-HPLC) using Waters 2695 Alliance system (Water Corporation, Milford Mass.) with a Corona charged aerosol detector (CAD) (ESA Biosciences, Inc, Chelmsford, Mass.). Individual lipids in RDVs are analyzed using an Agilent Zorbax SB-C18 (50×4.6 mm, 1.8 μm particle size) column with CAD at 60° C. The mobile phase is composed of A: 0.1% TFA in H$_2$O and B: 0.1% TFA in IPA. The gradient changes from 60% mobile phase A and 40% mobile phase B from time 0 to 40% mobile phase A and 60% mobile phase B at 1.00 min; 40% mobile phase A and 60% Mobile phase B from 1.00 to 5.00 min; 40% mobile phase A and 60% mobile phase B from 5.00 min to 25% mobile phase A and 75% mobile phase B at 10.00 min; 25% mobile phase A and 75% mobile phase B from 10.00 min to 5% mobile phase A and 95% mobile phase B at 15.00 min; and 5% mobile phase A and 95% mobile phase B from 15.00 to 60% mobile phase A and 40% mobile phase B at 20.00 min with flow rate of 1 ml/min. The individual lipid concentration is determined by comparing to the standard curve with all the lipid components in the RDVs with a quadratic curve fit. The molar percentage of each lipid is calculated based on its molecular weight.

Utilizing the above described LNP process, specific LNPs with the following ratios were identified:

Nominal Composition:
Cationic Lipid/Cholesterol/PEG-DMG 60/38/2
Cationic Lipid/Cholesterol/PEG-DMG 67.3/29/3.7.
Luc siRNA

```
                                        (SEQ. ID. NO.: 1)
5'-iB-AUAAGGCUAUGAAGAGAUATT-iB 3'

(SEQ. ID. NO.: 2)
3'-UUUAUUCCGAUACUUCUCUAU-5'
AUGC - Ribose
iB - Inverted deoxy abasic
UC - 2' Fluoro
AGT - 2' Deoxy
AGU - 2' OCH₃
```

Nominal Composition
Cationic Lipid /Cholesterol/PEG-DMG 60/38/2
Cationic Lipid/Cholesterol/PEG-DMG/DSPC 40/48/2/10
A poB siRNA (SEQ ID NO.: 3)
5'iB-*CUUU*AAC*AAUUCCU*GAAAUTT-iB (SEQ ID NO.: 4)
3'-UUGAAA*UU*G*UUA*AGGAC***UUUA*-5'
AUGC - Ribose
iB - Inverted deoxy abasic
*UC* - 2' Fluoro
AGT - 2' Deoxy
AG*U* - 2' OCH$_3$ The synthesis and use of oligonucleotides, in particular siRNA and miRNA, are known. (See US patent applications: US 2006/0083780, US 2006/0240554, US 2008/0020058, US 200910263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al., Rational design of cationic lipids for siRNA delivery, Nature Biotechnology, published online 17 Jan. 2010; doi: 10.1038/nbt.1602.

Example 1

Mouse In Vivo Evaluation of Efficacy

LNPs utilizing Compounds 1-4, in the nominal compositions described immediately above, were evaluated for in vivo efficacy and induction of inflammatory cytokines in a luciferase mouse model. The siRNA targets the mRNA transcript for the firefly (*Photinus pyralis*) luciferase gene (Accession #M15077). The primary sequence and chemical modification pattern of the luciferase siRNA is displayed above. The in vivo luciferase model employs a transgenic mouse in which the firefly luciferase coding sequence is present in all cells. ROSA26-LoxP-Stop-LoxP-Luc (LSL-Luc) transgenic mice licensed from the Dana Farber Cancer Institute are induced to express the Luciferase gene by first removing the LSL sequence with a recombinant Ad-Cre virus (Vector Biolabs). Due to the organo-tropic nature of the virus, expression is limited to the liver when delivered via tail vein injection. Luciferase expression levels in liver are quantitated by measuring light output, using an IVIS imager (Xenogen) following administration of the luciferin substrate (Caliper Life Sciences). Pre-dose luminescence levels are measured prior to administration of the RDVs. Luciferin in PBS (15 mg/mL) is intraperitoneally (IP) injected in a volume of 150 uL. After a four minute incubation period mice are anesthetized with isoflurane and placed in the IVIS imager. The RDVs (containing siRNA) in PBS vehicle were tail vein injected n a volume of 0.2 mL. Final dose levels ranged from 0.3 to 3 mg/kg siRNA. PBS vehicle alone was dosed as a control. Three hours post dose, mice were bled retro-orbitally to obtain plasma for cytokine analysis. Mice were imaged 48 hours post dose using the method described above. Changes in luciferin light output directly correlate with luciferase mRNA levels and represent an indirect measure of luciferase siRNA activity. In vivo efficacy results are expressed as % inhibition of luminescence relative to pre-dose luminescence levels. Plasma cytokine levels were determined using the SearchLight multiplexed cytokine chemoluminescent array (Pierce/Thermo). Systemic administration of the luciferase siRNA RDVs decreased luciferase expression in a dose dependent manner. Greater efficacy was observed in mice dosed with Compound 1 containing RDVs than with the RDV containing the octyl-CLinDMA (OCD) cationic lipid (FIG. 1). OCD is known and described in WO2010/021865.

Rat In Vivo Evaluation of Efficacy and Toxicity

Figure 2:
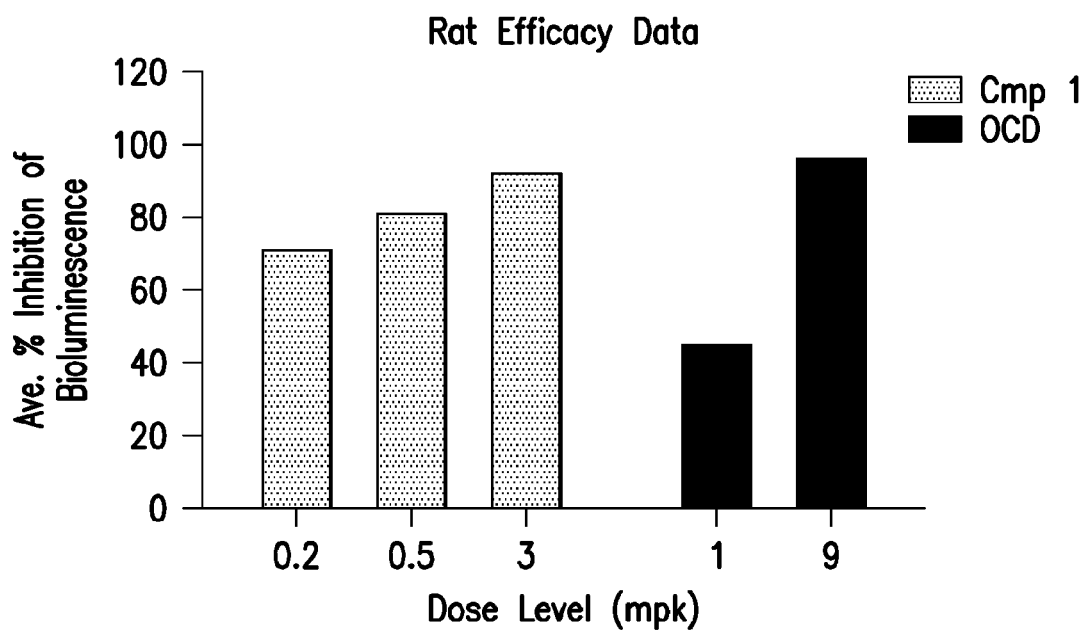
FIG. 2: LNP (Compound 1) efficacy in rat.

LNPs utilizing Compound 1 in the nominal compositions described above, were evaluated for in vivo efficacy and increases in alanine amino transferase and aspartate amino transferase in Sprague-Dawley (Crl:CD(SD) female rats (Charles River Labs). The siRNA targets the mRNA transcript for the ApoB gene (Accession #NM 019287). The primary sequence and chemical modification pattern of the ApoB siRNA is displayed above. The RDVs (containing siRNA) in PBS vehicle were tail vein injected in a volume of 1 to 1.5 mL. Infusion rate is approximately 3 ml/min. Five rats were used in each dosing group. After LNP administration, rats are placed in cages with normal diet and water present. Six hours post dose, food is removed from the cages. Animal necropsy is performed 24 hours after LNP dosing. Rats are anesthetized under isoflurane for 5 minutes, then maintained under anesthesia by placing them in nose cones continuing the delivery of isoflurane until ex-sanguination is completed. Blood is collected from the vena cava using a 23 guage butterfly venipuncture set and aliquoted to serum separator vacutainers for serum chemistry analysis. Punches of the excised caudate liver lobe are taken and placed in RNALater (Ambion) for mRNA analysis. Preserved liver tissue was homogenized and total RNA isolated using a Qiagen bead mill and the Qiagen miRNA-Easy RNA isolation kit following the manufacturer's instructions. Liver ApoB mRNA levels were determined by quantitative RT-PCR. Message was amplified from purified RNA utilizing a rat ApoB commercial probe set (Applied Biosystems Cat #RN01499054_ml). The PCR reaction was performed on an ABI 7500 instrument with a 96-well Fast Block. The ApoB mRNA level is normalized to the housekeeping PPIB (NM 011149) mRNA. PPM mRNA levels were determined by RT-PCR using a commercial probe set (Applied Biosystems Cat. No. Mm00478295_m1). Results are expressed as a ratio of ApoB mRNA/PPIB mRNA. All mRNA data is expressed relative to the PBS control dose. Serum ALT and AST analysis were performed on the Siemens Advia 1800 Clinical Chemistry Analyzer utilizing the Siemens alanine aminotransferase (Cat #03039631) and aspartate aminotransferase (Cat #03039631) reagents. Greater efficacy was observed in rats dosed with Compound 1 containing RDV than with the RDV containing the octyl-CLinDMA (OCD) cationic lipid (FIG. 2).

What is claimed is:

1. A cationic lipid of Formula A:

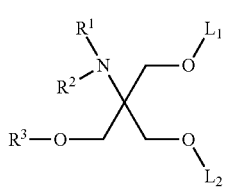

A wherein:

$R^1$ and $R^2$ are independently selected from methyl, ethyl and propyl, wherein said methyl, ethyl and propyl is optionally substituted with one to three substituents selected from R';

$R^3$ is selected from H, methyl, ethyl and propyl;

R' is independently selected from halogen, R", OR", SR", CN, $CO_2R''$ and $CON(R'')_2$;

R" is independently selected from H and $(C_1$-$C_6)$alkyl, wherein said alkyl is optionally substituted with halogen and OH;

$L_1$ is selected from $C_4$-$C_{22}$ alkyl and $C_4$-$C_{22}$ alkenyl, said alkyl and alkenyl are optionally substituted with R'; and $L_2$ is selected from $C_4$-$C_{22}$ alkyl and $C_4$-$C_{22}$ alkenyl, said alkyl and alkenyl are optionally substituted with R';

or any pharmaceutically acceptable salt or stereoisomer thereof.

2. A cationic lipid of Formula A according to claim 1, wherein:

$L_1$ is $C_4$-$C_{22}$ alkenyl.

3. A lipid nanoparticle comprising a cationic lipid according to claim 1.

4. The lipid nanoparticle of claim 3, wherein the nanoparticle comprises oligonucleotides.

5. The lipid nanoparticle of claim 4 wherein the oligonucleotides are siRNA or miRNA.

6. The lipid nanoparticle of claim 5 wherein the oligonucleotides are siRNA.

7. The lipid nanoparticle of claim 4, wherein the lipid nanoparticle comprises cholesterol and PEG-DMG.

8. The lipid nanoparticle of claim 7, wherein the lipid nanoparticle further comprises DSPC.

* * * * *